(12) United States Patent
Yamakita

(10) Patent No.: US 8,599,386 B2
(45) Date of Patent: Dec. 3, 2013

(54) OPTICAL TOMOGRAPHIC IMAGING APPARATUS, INTERFERENCE SIGNAL PROCESSING METHOD, AND ENDOSCOPE APPARATUS

(75) Inventor: Hiroshi Yamakita, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 341 days.

(21) Appl. No.: 12/973,193

(22) Filed: Dec. 20, 2010

(65) Prior Publication Data

US 2011/0149291 A1     Jun. 23, 2011

(30) Foreign Application Priority Data

Dec. 21, 2009   (JP) .................................. 2009-289211

(51) Int. Cl.
*G01B 11/02*     (2006.01)

(52) U.S. Cl.
USPC .......................................... 356/497; 356/479

(58) Field of Classification Search
USPC .................................. 356/479, 497, 484, 489
See application file for complete search history.

(56) References Cited

U.S. PATENT DOCUMENTS

| | | | |
|---|---|---|---|
| 7,391,520 B2 * | 6/2008 | Zhou et al. ..................... | 356/479 |
| 7,830,524 B2 | 11/2010 | Teramura et al. | |
| 2005/0280828 A1 * | 12/2005 | Fitzgerald de Boer ....... | 356/497 |
| 2007/0002327 A1 | 1/2007 | Zhou et al. | |
| 2007/0232861 A1 | 10/2007 | Kohno et al. | |
| 2008/0117427 A1 * | 5/2008 | Teramura et al. ............ | 356/484 |

FOREIGN PATENT DOCUMENTS

| | | |
|---|---|---|
| JP | 2006-47264 A | 2/2006 |
| JP | 2007-163241 A | 6/2007 |
| JP | 2007-268047 A | 10/2007 |
| JP | 2008-128708 A | 6/2008 |
| JP | 2008-261768 A | 10/2008 |

\* cited by examiner

*Primary Examiner* — Tarifur Chowdhury
*Assistant Examiner* — Jonathan Hansen
(74) *Attorney, Agent, or Firm* — Birch, Stewart, Kolasch & Birch, LLP

(57) ABSTRACT

An interference signal processing method includes: dividing, into a measuring light beam and a reference light beam, each of a plurality of luminous fluxes which respectively have predetermined wavelength bands different from each other and which are emitted by sweeping the wavelength in the respective predetermined wavelength bands; detecting, for each of the luminous fluxes, an interference light signal between the reference light beam and a reflected light beam which is reflected from a measuring object at the time when the plurality of measuring light beams are irradiated onto the measuring object; calculating at least phase information of a plurality of detected interference light signals; and using, as a reference, the phase of the interference light signal obtained from the luminous flux of a first wavelength band, and of generating a corrected interference light signal by correcting, based on the phase information, the phase of the interference light signals obtained from the luminous fluxes of the plurality of wavelength bands different from the first wavelength band.

11 Claims, 12 Drawing Sheets

OPTICAL TOMOGRAPHIC IMAGING APPARATUS, INTERFERENCE SIGNAL PROCESSING METHOD, AND ENDOSCOPE APPARATUS

BACKGROUND OF THE INVENTION

1. Field of the Invention

The presently disclosed subject matter relates to an optical tomographic imaging apparatus, an interference signal processing method, and an endoscope apparatus. More particularly, the presently disclosed subject matter relates to an optical tomographic imaging apparatus configured to generates an optical tomographic image by OCT (Optical Coherence Tomography) measurement, an interference signal processing method used in the optical tomographic imaging apparatus, and an endoscope apparatus used together with the optical tomographic imaging apparatus.

2. Description of the Related Art

Conventionally, it has been proposed that, when an optical tomographic image of a living tissue is obtained, an optical tomographic image obtaining apparatus using OCT measurement is used. In addition to the case where tomographic images of the ocular fundus, the anterior ocular segment, and the skin are obtained, the optical tomographic image obtaining apparatus is applied to observation of various parts, such as observation of an arterial vascular wall performed by using an OCT probe (optical probe), and observation of a digestive organ performed by inserting the OCT probe through a forceps channel of an endoscope. In the optical tomographic image obtaining apparatus, after a low coherent light beam emitted from a light source is divided into a measuring light beam and a reference light beam, a light beam, which is reflected or back scattered by a measuring object at the time when the measuring light beam is irradiated onto the measuring object, is multiplexed with the reference light beam, and an optical tomographic image is obtained based on the intensity of the interference light beam between the reflected light beam and the reference light beam. In the following, the reflected light beam and the back scattered light beam from the measuring object are collectively expressed as a reflected light beam.

The above described OCT measurement is roughly classified into the TD-OCT (Time domain OCT) measurement and the FD-OCT (Fourier Domain OCT) measurement. The TD-OCT (Time domain OCT) measurement is a method that, while changing the optical path length of a reference light beam, measures the intensity of an interference light beam, and thereby obtains the intensity distribution of reflected light beams which corresponds to positions in the depth direction (hereinafter referred to as depth positions) of a measuring object.

On the other hand, the FD-OCT (Fourier Domain OCT) measurement is a method that, without changing the optical path lengths of a reference light beam and a signal light beam, measures the intensity of an interference light beam for each spectral component of the light beam, and performs, by using a computer, frequency analysis, as represented by Fourier transform, for the spectral interference intensity signals obtained here, so as to thereby obtain the intensity distribution of reflected light beams which corresponds to the depth positions of a measuring object. In recent years, the FD-OCT measurement has been attracting attention as a method for enabling high-speed measurement, because the mechanical scanning needed for the TD-OCT is not necessary in the FD-OCT measurement. As typical apparatus configurations for performing the FD (Fourier Domain)-OCT measurement, it is possible to list two types of apparatuses based on SD-OCT (Spectral Domain OCT) and SS-OCT (Swept source OCT).

The OCT measuring technique is highly expected to be applied, in particular, to the optical biopsy (biopsy) in which a lesion region is located by non-invasive cell level measurement. However, the resolution of the OCT is about 10 μm at present, and is insufficient for the observation at the level of cell size of 10 to 20 μm. Thus, it is desired to improve the resolution of the OCT.

The axial resolution of OCT:Δz is determined by the following expression (1) using the spectral width and the center wavelength of a light source used in the OCT.

$$\Delta z = (2 \cdot \ln 2/\pi) \cdot (\lambda^2/\Delta\lambda) \quad (1)$$

where $\Delta\lambda$ is the spectral width, and $\lambda$ is the center wavelength.

In order to improve the resolution of OCT, it is necessary to expand the spectral width of the light source. Thus, research and development of a Ti:sapphire light source, and the like, have been promoted. However, these wide band light sources at present have disadvantages that their cost is high and that they are not suitable for mass production.

In order to solve these problems, in recent years, it has been investigated to improve the resolution of OCT in such a way that a wide band light source is produced in a pseudo manner by using SLDs having a plurality of wavelength bands. However, this method for increasing the band width of the light source in the pseudo manner has a problem that the SLD light sources, which are generally used for diagnosing a living body and which have the center wavelengths of 1.0 μm and the 1.3 μm, cannot cover all the spectral bands and hence the spectral bands are separated from each other. Thus, an interference signal is discontinuously divided due to the separation between spectral bands, so that an artifact is caused in an OCT image. In particular, a signal obtained in the TD system becomes an OCT image itself, and hence it is difficult to prevent the generation of the artifact.

Thus, multiplexing OCT techniques using the FD system are disclosed, for example, in the following patent documents.

Japanese Patent Application Laid-Open No. 2008-128708 discloses a multiplexing OCT technique which combines a plurality of multiplexing OCT systems using a plurality of light sources.

Japanese Patent Application Laid-Open No. 2008-261768 discloses a multiplexing OCT technique which uses an average value and a weighted average value to estimate, from an interference signal obtained from a spectrum having spectral bands separated from each other, an interference signal at the central part of the spectrum.

Japanese Patent Application Laid-Open No. 2006-47264 discloses a multiplexing OCT technique by which the output of a variable wavelength light source in a multiplexing OCT system using a plurality of light sources is monitored for multiplication correction.

SUMMARY OF THE INVENTION

However, Japanese Patent Application Laid-Open No. 2008-128708 and Japanese Patent Application Laid-Open No. 2008-261768 disclose a multiplexing OCT technique which estimates the information between the divided spectra and which uses an average value and a weighted average value of each of the divided spectra. However, in the multiplexing OCT technique, when the average values are practically used to obtain interference signals, the phases of the interference signals become discontinuous, so that an artifact is caused (generated).

In particular, the multiplexing OCT technique disclosed in Japanese Patent Application Laid-Open No. 2008-128708 has problems that temporal and spatial mismatches, which are caused between the interference signals of the respective different OCT systems at the time when the systems are combined to each other, are not considered at all and cause an artifact, and that the positioning of the respective systems needs to be performed with very high precision in order to prevent the generation of the artifact. On the other hand, the multiplexing OCT technique disclosed in Japanese Patent Application Laid-Open No. 2008-261768 has a problem that, when the processing to estimate the intermediate spectra is actually performed by using the average value, and the like, the phases of two interference signals do not match each other, so that an artifact is caused.

Further, Japanese Patent Application Laid-Open No. 2006-47264 discloses the multiplexing OCT technique used in a system which obtains a tomogram by using light beams having a plurality of wavelengths, and in which the intensity of interference signal is monitored for multiplication correction. However, although the generation of artifact can be suppressed in an ideal state in the system disclosed in Japanese Patent Application Laid-Open No. 2006-47264, it is impossible, in view of the practical precision, to adjust the intensity of interference signal in the order of the phase of the respective light sources. That is, in the ideal state, it is possible to prevent the generation of artifact by the multiplication correction of the intensity signals of the two light sources. However, in practice, the intensity signals need to be adjusted in the order (several nm) of the phase of the light sources.

The presently disclosed subject matter has been made in view of the above described circumstances. An object of the presently disclosed subject matter is to provide an optical tomographic imaging apparatus which can obtain, without the generation of artifact, a highly precise OCT image by using an interference signal obtained from a plurality of light sources, and to provide an interference signal processing method used in the optical tomographic imaging apparatus, and an endoscope used together with the optical tomographic imaging apparatus.

To this end, a first aspect of the presently disclosed subject matter provides an optical tomographic imaging apparatus including: a light source unit configured to emit a plurality of luminous fluxes respectively having predetermined wavelength bands different from each other by sweeping wavelength in each of the predetermined bands; a light dividing device configured to divide, into a measuring light beam and a reference light beam, each of the plurality of luminous fluxes emitted from the light source unit; a plurality of interference light detecting devices, when a plurality of measuring light beams divided by the light dividing device are irradiated onto a measuring object, each of the plurality of interference light detecting devices detecting, for each of the luminous fluxes, an interference light signal between a reflected light beam from the measuring object and the reference light beam; an interference information calculating device configured to calculate at least phase information of the plurality of interference signals detected by the interference light detecting devices; and an interference information correcting device configured to use, as a reference, the phase of the interference light signal obtained from the luminous flux of a first wavelength band, and to generate a corrected interference light signal by correcting, based on the phase used as the reference, the phase of the interference light signal obtained from the luminous flux of a wavelength band different from the first wavelength band.

In the optical tomographic imaging apparatus according to the first aspect of the presently disclosed subject matter, the interference information calculating device calculates at least the phase information of the plurality of interference light signals detected by the interference detecting devices. Further, the interference information correcting device uses, as a reference, the phase of the interference light signal obtained from the luminous flux of a first wavelength band, and generates a corrected interference light signal by correcting, based on the phase used as the reference, the phase of the interference light signal obtained from the luminous flux of a wavelength band different from the first wavelength band. Thereby, a highly precise OCT image can be obtained without the generation of artifact by using the interference signals obtained from the plurality of light sources.

A second aspect of the presently disclosed subject matter provides an optical tomographic imaging apparatus according to the first aspect, further including: a corrected composite signal generating device configured to generate a corrected composite signal formed by combining the interference light signal of the first wavelength band and the corrected interference light signal; and a tomographic image information generating device configured to generate tomographic image information of the measuring object based on the corrected composite signal.

A third aspect of the presently disclosed subject matter provides an optical tomographic imaging apparatus according to the second aspect, further including a composite interference signal generating device configured to generate a composite interference signal formed by combining the plurality of interference light signals detected by the interference light detecting devices, wherein the interference information calculating device calculates the phase information based on the composite interference signal.

A fourth aspect of the presently disclosed subject matter provides an optical tomographic imaging apparatus according to the third aspect, wherein the interference information calculating device calculates signal intensity information of the interference light signal based on the composite interference signal.

A fifth aspect of the presently disclosed subject matter provides an optical tomographic imaging apparatus according to the fourth aspect, further including an intensity correcting device configured to correct the envelope of the signal intensity of the corrected composite signal to a Gaussian shape based on the signal intensity information of the interference light signal, the signal intensity information being calculated by the interference information calculating device.

A sixth aspect of the presently disclosed subject matter provides an optical tomographic imaging apparatus according to any one of the third to fifth aspects, further including a signal dividing device configured to divide each of the interference signal and the composite interference signal based on predetermined divided wavelength widths, wherein the interference information calculating device calculates the phase information for each of the divided wavelength widths, wherein the interference information correcting device generates the corrected interference light signal for each of the divided wavelength widths, and wherein the corrected composite signal generating device generates the corrected composite signal for each of the divided wavelength widths.

A seventh aspect of the presently disclosed subject matter provides an optical tomographic imaging apparatus according to any one of the first to sixth aspects, wherein the wavelength sweep periods are synchronized between the plurality of luminous fluxes.

An eighth aspect of the presently disclosed subject matter provides an interference signal processing method of an optical tomographic imaging apparatus including: a light beam dividing step of dividing, into a measuring light beam and a reference light beam, each of a plurality of luminous fluxes which respectively have predetermined wavelength bands different from each other and which are emitted by sweeping the wavelength in the respective predetermined wavelength bands; an interference light detecting step of detecting, for each of the luminous fluxes, an interference light signal between the reference light beam and a reflected light beam which is reflected from a measuring object at the time when the plurality of measuring light beams formed in the light beam dividing step are irradiated onto the measuring object; an interference information calculating step of calculating at least phase information of a plurality of interference light signals detected in the interference light detecting step; and an interference information correcting step of using, as a reference, the phase of the interference light signal obtained from the luminous flux of a first wavelength band, and of generating a corrected interference light signal by correcting, based on the phase information, the phase of the interference light signals obtained from the luminous fluxes of the plurality of wavelength bands different from the first wavelength band.

A ninth aspect of the presently disclosed subject matter provides an endoscope apparatus including: the optical tomographic imaging apparatus according to any one of the first to seventh aspects; and an endoscope having a treatment instrument channel (forceps channel) into which an optical probe for guiding the measuring light beam into a body cavity is inserted.

As described above, according to the presently disclosed subject matter, it is possible to obtain an effect that a highly precise OCT image can be obtained without or decreasing the generation of artifact by using interference signals obtained from a plurality of light sources.

DETAILED DESCRIPTION OF THE PREFERRED EMBODIMENTS

In the following, an optical tomographic imaging apparatus, an interference signal processing method, and an endoscope apparatus according to the presently disclosed subject matter will be described in detail with reference to the accompanying drawings.

Figure 1:
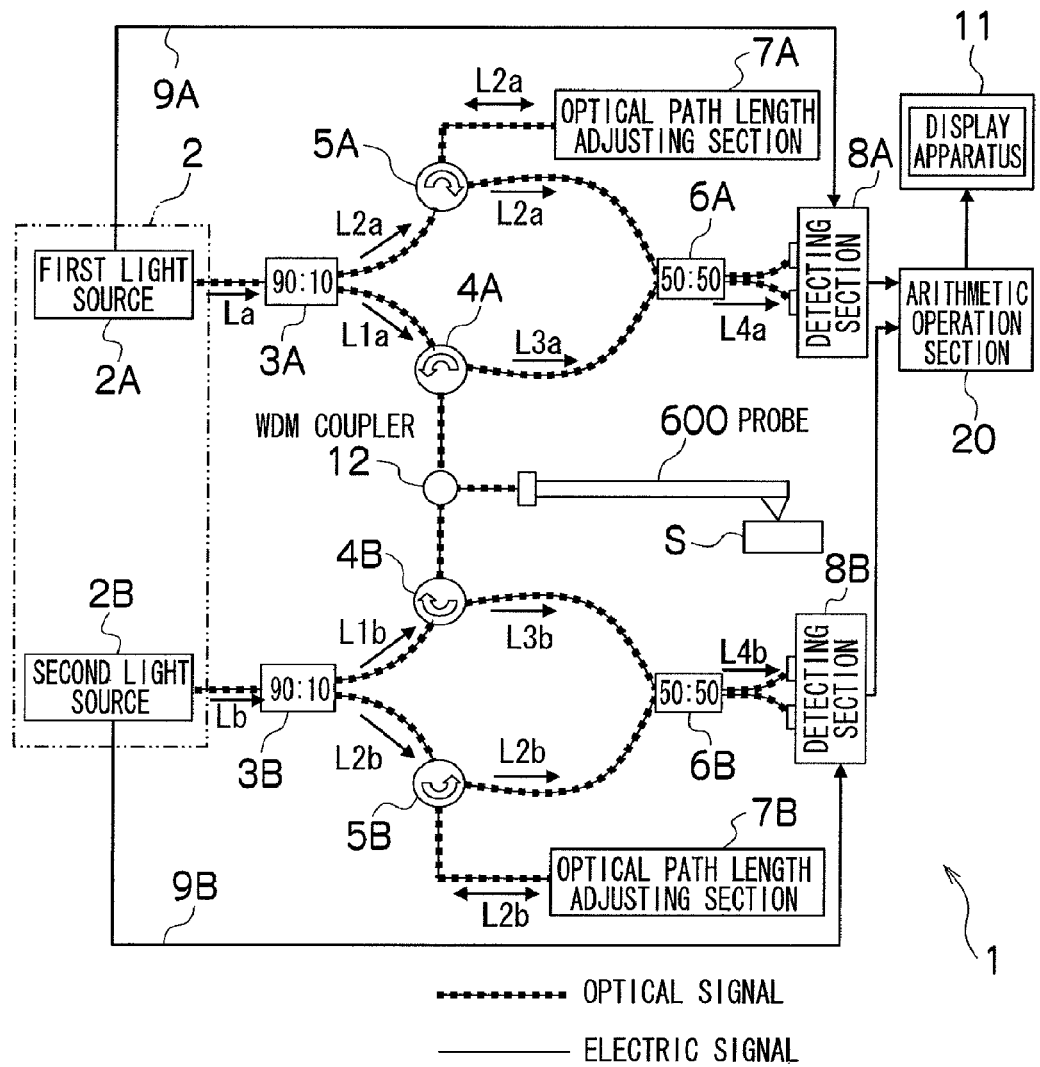
FIG. 1 is a schematic diagram illustrating a preferred embodiment of an optical tomographic imaging apparatus.
Figure 2:
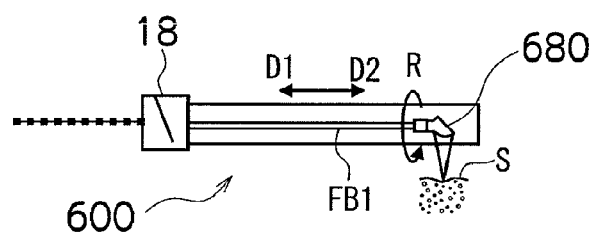
FIG. 2 illustrates a configuration of a major portion of the OCT probe illustrated in FIG. 1.

FIG. 1 is a schematic diagram illustrating a preferred embodiment of an optical tomographic imaging apparatus. FIG. 2 illustrates a configuration of a major portion of the OCT probe illustrated in FIG. 1.

An optical tomographic imaging apparatus 1 of the present embodiment is configured to obtain a tomographic image of a measuring object, such as, for example, a living tissue and a cell in a body cavity, by SS-OCT (Swept source OCT) measurement. As illustrated in FIG. 1, the optical tomographic imaging apparatus 1 is configured by including a light source unit 2, light dividing sections 3A and 3B as light dividing devices, multiplexing sections 6A and 6B, interference light detecting sections 8A and 8B as interference light detecting devices, an arithmetic operation section 20 as an interference information calculating device and an interference information correcting device, and a display apparatus 11. Note that, the arithmetic operation section 20 is configured, for example, by a personal computer, and the like.

The light source unit 2 emits a plurality of luminous fluxes having mutually separated wavelength bands $\Delta\lambda a$ and $\Delta\lambda b$. Specifically, the light source unit 2 has a first light source 2A which emits a laser light beam while sweeping the wavelength in the wavelength band $\Delta\lambda a$ at a fixed period, and a second light source 2B which emits a laser light beam while sweeping the wavelength in the wavelength band $\Delta\lambda b$ at the fixed period. Therefore, when the light sources 2A and 2B sweep the wavelength for one period, the light sources 2A and 2B emit luminous fluxes La and Lb having the wavelength bands $\Delta\lambda a$ and $\Delta\lambda b$, respectively.

Each of the light dividing sections 3A and 3B is configured, for example, by a 2×2 optical coupler having a branching ratio of 90:10. The light dividing section 3A divides the luminus flux La into a measurement light beam L1a and a reference light beam L2a. The light dividing section 3B divides the luminous flux Lb into a measurement light beam L1b and a reference light beam L2b. At this time, the light dividing sections 3A and 3B respectively divides the luminous fluxes La and Lb at a ratio of the measurement light beam:the reference light beam=90:10. Here, the measuring light beams L1a and L1b are respectively guided to an OCT probe 600 via circulators 4A and 4B and a multiplexing/demultiplexing section 12.

The OCT probe 600 guides the measuring light beams L1a and L1b made incident thereon via an optical rotary connector 18 to a measuring object S and simultaneously irradiates the measuring light beams L1a and L1b onto the same region of the measuring object S. Further, the OCT probe 600 guides reflected beams L3a and L3b which are reflected from the measuring object S at the time when the measuring light beams L1a and L1b are irradiated onto the measuring object S.

Note that as illustrated in FIG. 2, the OCT probe 600 is configured such that a fiber section FB1 having a ball lens 680 at the distal end thereof is connected to the optical rotary connector 18 so as to be rotated by a motor (not illustrated). Thereby, the OCT probe 600 scans the luminous flux on the measuring object S radially in the circumferential direction (illustrated by the arrow R in FIG. 2), so that a two-dimensional tomographic image can be measured. Further, the OCT probe 600 can also measure a three-dimensional tomographic image in such a manner that the distal end of the OCT probe 600 is moved back and forth for scanning by a motor (not illustrated) in the direction (illustrated by the arrows D1 and D2 in FIG. 2) perpendicular to the plane formed by the scanning circle of the optical path.

Returning to FIG. 1, in the optical tomographic imaging apparatus 1, the multiplexing/demultiplexing section 12 is provided on the optical path between the light dividing section 3A and the OCT probe 600, and on the optical path between the light dividing section 3B and the OCT probe 600. The multiplexing/demultiplexing section 12 has a function of multiplexing and demultiplexing light beams according to a set cutoff wavelength, and is configured, for example, by a WDM (Wavelength Division Multiplexing) coupler.

The multiplexing/demultiplexing section 12 multiplexes the measuring light beams L1a and L1b respectively made incident thereon from the light dividing sections 3A and 3B, so as to emit a multiplexed light beam to the side of the OCT probe 600. The multiplexing/demultiplexing section 12 demultiplexes reflected light beams L3a and L3b made incident thereon from the side of the OCT probe 600, so as to respectively emit demultiplexed light beams to the sides of the multiplexing sections 6A and 6B.

The reflected light beam L3a is multiplexed with the reference light beam L2a in the multiplexing section 6A, and the reflected light beam L3b is multiplexed with the reference light beam L2b in the multiplexing section 6B.

Note that a reflection type optical path length adjusting section 7A is provided in the optical path of the reference light beam L2a from the light dividing section 3A to the multiplexing section 6A via a circulator 5A, and a reflection type optical path length adjusting section 7B is provided in the optical path of the reference light beam L2b from the light dividing section 3B to the multiplexing section 6B via a circulator 5B. The optical path length adjusting sections 7A and 7B respectively change the optical path lengths of the reference light beams L2a and L2b in order to adjust the position where the acquisition of a tomographic image is started.

Each of the multiplexing sections 6A and 6B is configured, for example, by a 2×2 optical fiber coupler having a branching ratio of 50:50. The multiplexing section 6A multiplexes the reflected light beam L3a with the reference light beam L2a, and emits an interference light beam L4a generated at this time to the interference light detecting section 8A. The multiplexing section 6B multiplexes the reflected light beam L3b with the reference light beam L2b, and emits an interference light beam L4b generated at this time to the interference light detecting section 8B.

Note that in the optical tomographic imaging apparatus 1, the interference light beams L4a and L4b are respectively bisected by the multiplexing sections 6A and 6B, so that the bisected light beams of each of the interference light beams L4a and L4b are emitted to each of the interference light detecting sections 8A and 8B. The bisected light beams of each of the interference light beams L4a and L4b are balance-detected by using two photo detectors in each of the interference light detecting sections 8A and 8B. According to this balance detection mechanism, the influence of light intensity fluctuation can be suppressed and a clearer image can be obtained.

The interference light detecting sections 8A and 8B respectively have functions in which the interference light beams L4a and the L4b are respectively photoelectrically converted, so as to be respectively detected as a plurality of interference signals ISa and ISb respectively corresponding to the wavelength bands $\Delta\lambda$a and $\Delta\lambda$b of the luminous fluxes La and Lb. Here, the interference light detecting sections 8A and 8B respectively recognize the corresponding luminous fluxes by respectively synchronizing itself with the light sources 2A and 2B based on trigger signals 9A and 9B for wavelength sweep which are transmitted from the light sources 2A and 2B. At this time, interference signals ISa and ISb respectively corresponding to the luminous fluxes La and Lb are observed in the interference light detecting sections 8A and 8B, respectively. The interference signals ISa and ISb are outputted to the arithmetic operation section 20.

Then, in the arithmetic operation section 20, the interference signals ISa and ISb are subjected to signal processing, so that a tomographic image is displayed in the display apparatus 11.

Figure 3:
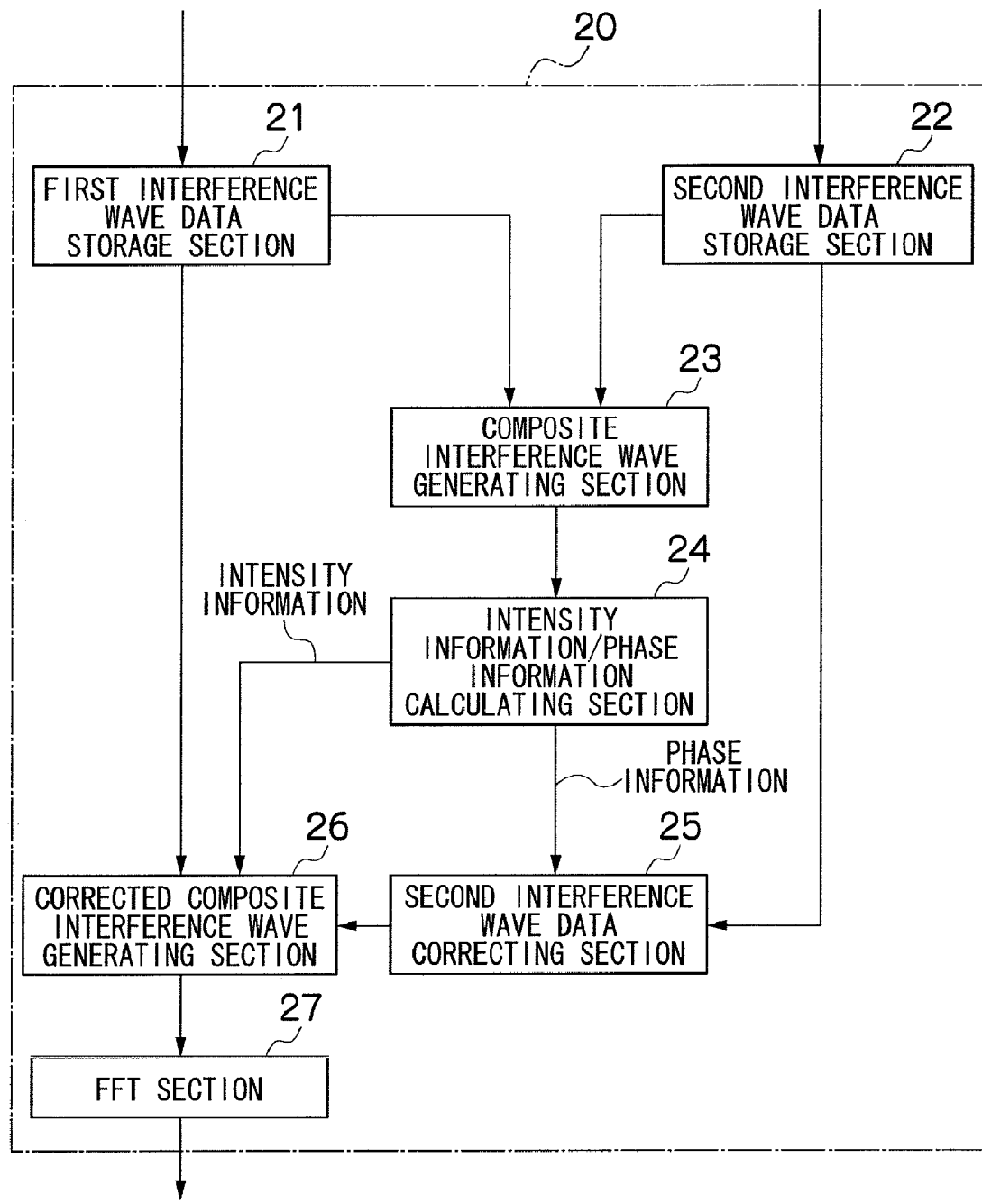
FIG. 3 is a block diagram illustrating a configuration of the arithmetic operation section illustrated in FIG. 1.

FIG. 3 is a block diagram illustrating a configuration of the arithmetic operation section illustrated in FIG. 1. As illustrated in FIG. 3, the arithmetic operation section 20 of the optical tomographic imaging apparatus 1 is configured by including: a first interference wave data storage section 21; a second interference wave data storage section 22; a composite interference wave generating section 23 as a composite interference signal generating device; an intensity information/phase information calculating section 24 as an interference information calculating device; a second interference wave data correcting section 25 as an interference information correcting device; a corrected composite interference wave generating section 26 as a corrected composite signal generating device; and an FFT section 27 as a tomogram information generating device.

The first interference wave data storage section 21 stores the digital data of the interference signal ISa, and the second interference wave data storage section 22 stores the digital data of the interference signal ISb.

The composite interference wave generating section 23 combines, for each of the wavelength bands, the digital data of the interference signal ISa stored in the first interference wave data storage section 21, with the digital data of the interference signal ISb stored in the second interference wave data storage section 22, and generates a composite interference wave (composite interference signal).

The intensity information/phase information calculating section 24 calculates, as phase information, a phase difference of the second interference wave data with respect to the first interference wave data from the composite interference wave generated by the composite interference wave generating section 23, and calculates the intensity information of the envelope of the composite interference wave.

The second interference wave data correcting section 25 corrects the second interference wave data into a corrected interference light signal by performing correction to shift the phase of the second interference wave data based on the phase information calculated by the intensity information/phase information calculating section 24, so as to make the phases of the interference signals ISa and ISb continuous.

The corrected composite interference wave generating section 26 combines, for each of the wavelength bands, the first interference wave data stored in the first interference wave data storage section 21 with the second interference wave data corrected by the second interference wave data correcting section 25, so as to generate a corrected composite interference wave (corrected composite signal). Note that, as will be described below, the corrected composite interference wave generating section 26 corrects the envelope (signal intensity) of the corrected composite interference wave based on the intensity information calculated by the intensity information/phase information calculating section 24.

The FFT section 27 performs fast Fourier transform (FFT) of the corrected composite interference wave generated by the corrected composite interference wave generating section 26, and generates tomographic image information (OCT image) of the measuring object S, so as to make the OCT image displayed in the display apparatus 11.

Next, the arithmetic operation section 20 in the optical tomographic imaging apparatus 1 according to the present embodiment configured as described above will be described.

(1) Phase correction:

As described above, an OCT image can be obtained by performing Fourier transform of the interference signal between the reference light beam and the measuring light beam.

Figure 4:
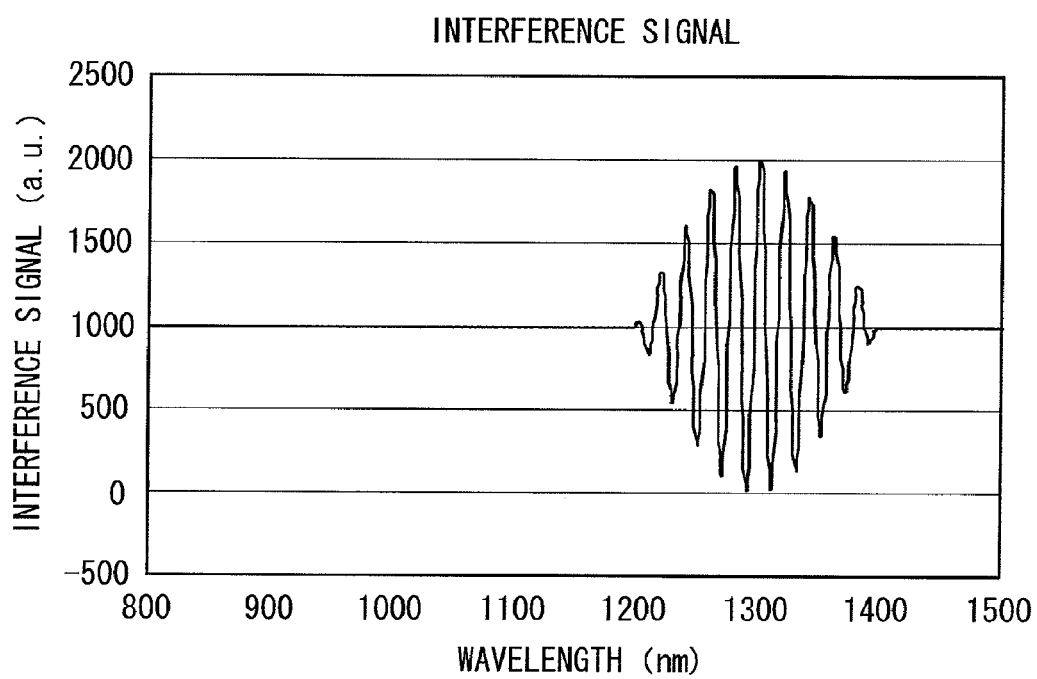
FIG. 4 illustrates a model waveform of an interference signal in the case where the light source illustrated in FIG. 1 has a narrow band spectrum.
Figure 5:
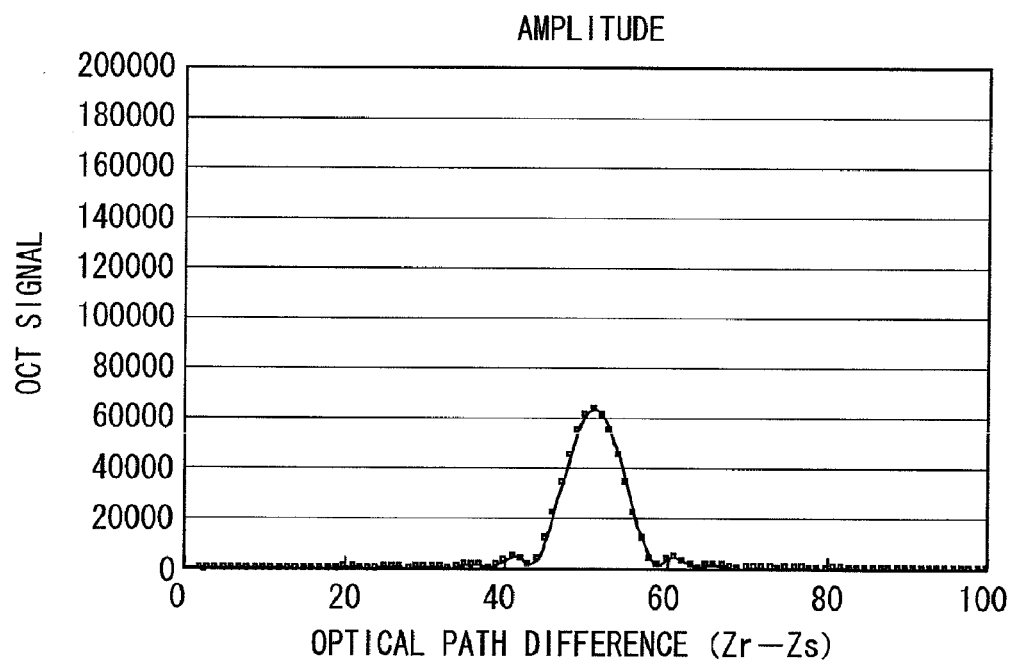
FIG. 5 illustrates an OCT signal of the model waveform of the interference signal illustrated in FIG. 4.
Figure 6:
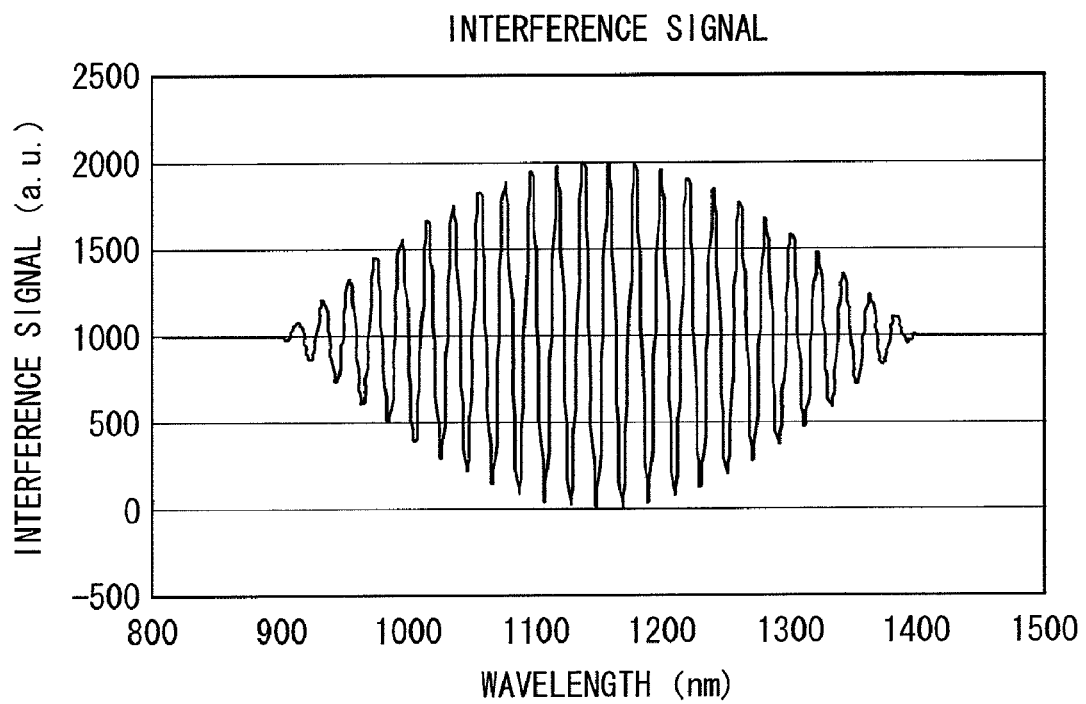
FIG. 6 illustrates a model waveform of an interference signal in the case where the light source illustrated in FIG. 1 has a wide band spectrum.
Figure 7:
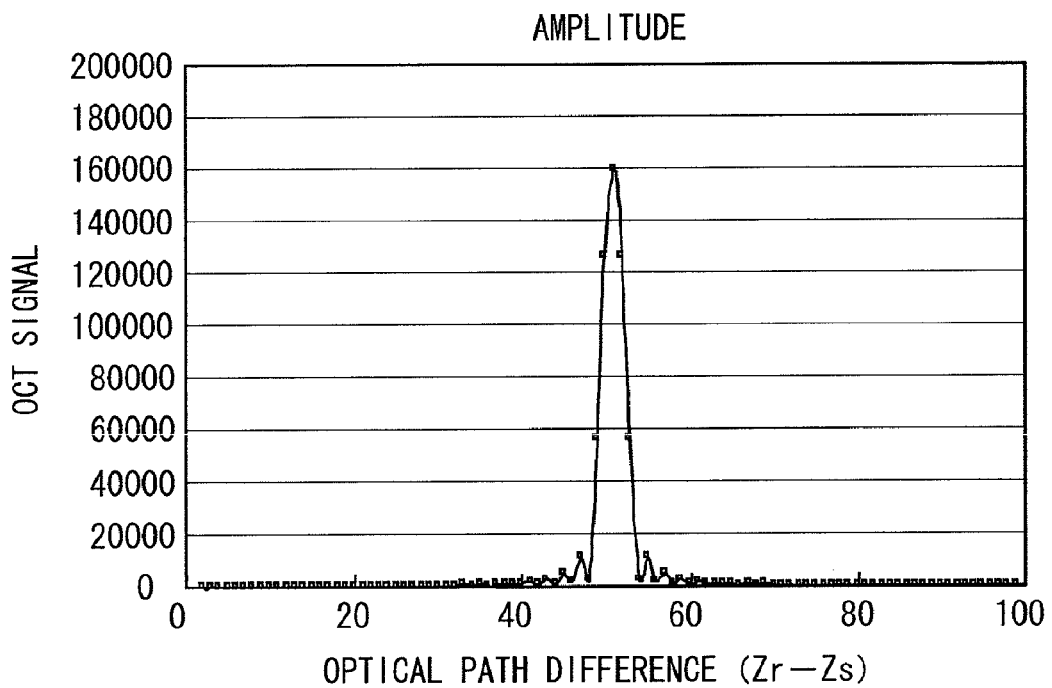
FIG. 7 illustrates an OCT signal of the model waveform of the interference signal illustrated in FIG. 6.
Figure 8:
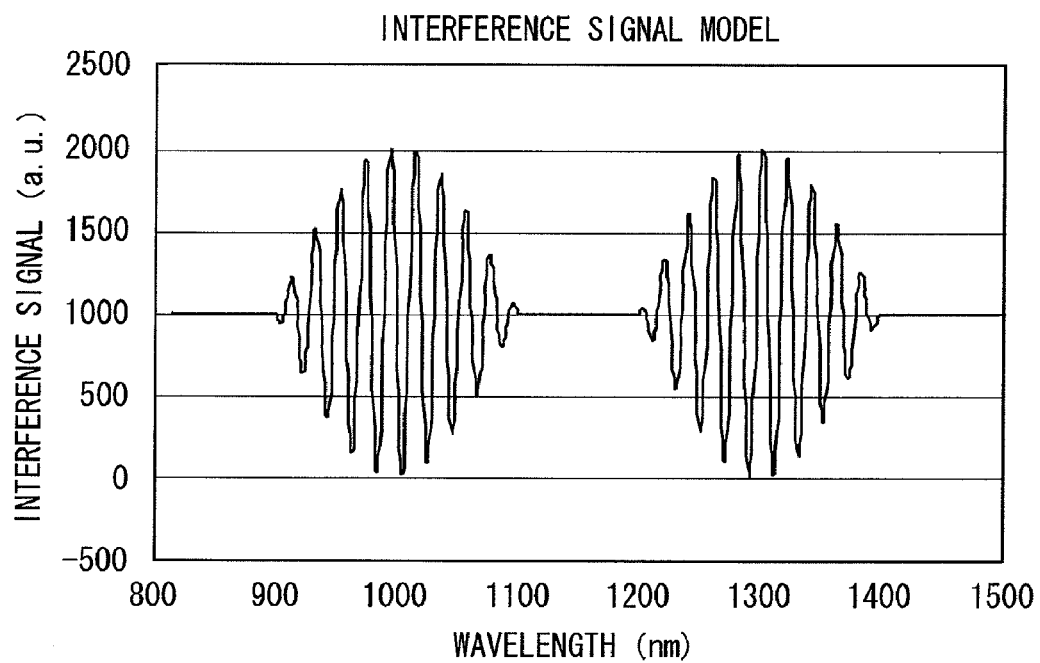
FIG. 8 illustrates a model waveform of an interference signal in the case where the light source illustrated in FIG. 1 has two narrow band spectra separated from each other.
Figure 9:
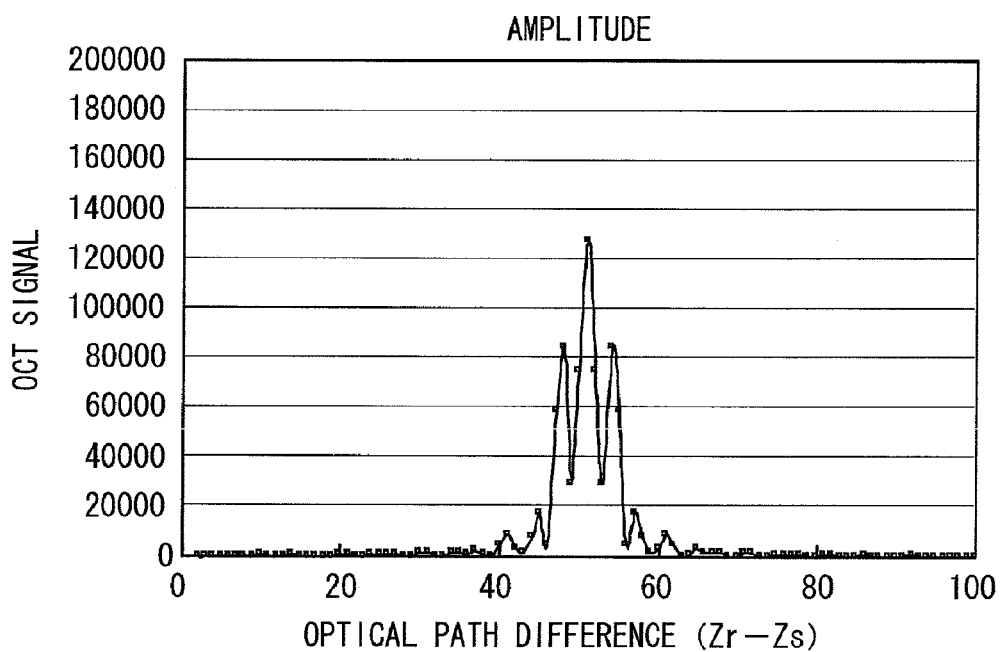
FIG. 9 illustrates a model waveform of an OCT signal in case where the phase difference between the two light source spectra illustrated in FIG. 8 is 0.
Figure 10:
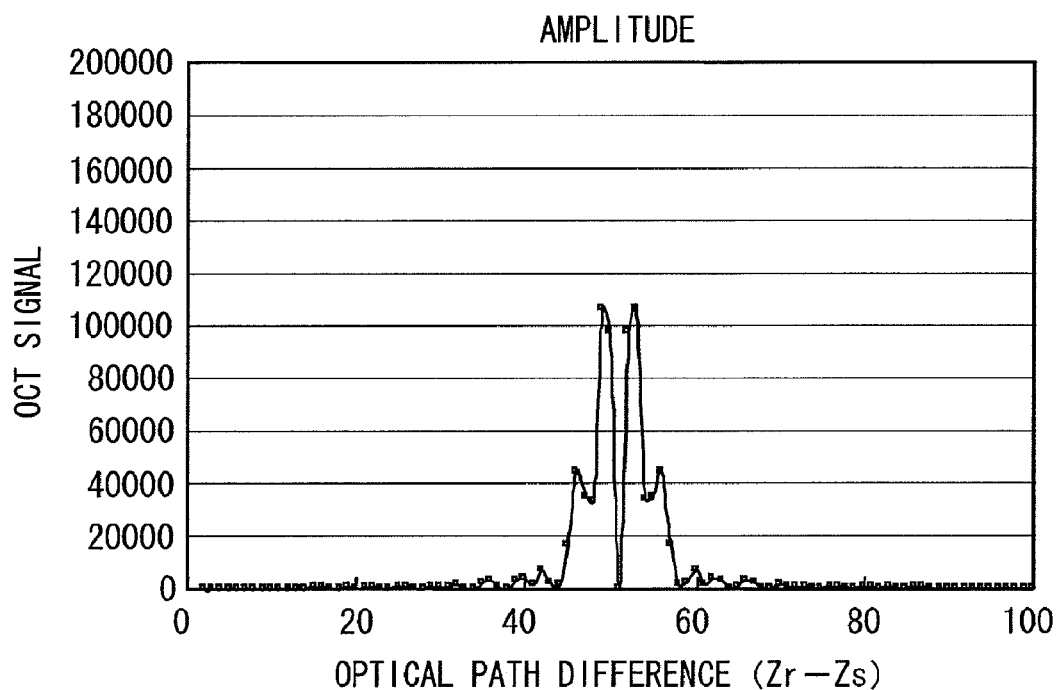
FIG. 10 illustrates a model waveform of an OCT signal in case where the phase difference between the two light source spectra illustrated in FIG. 8 is π.

FIG. 4 and FIG. 5 respectively illustrate model waveforms of an interference signal and an OCT signal in the case where the light source illustrated in FIG. 1 has a narrow band spectrum. FIG. 6 and FIG. 7 respectively illustrate model waveforms of an interference signal and an OCT signal in the case where the light source illustrated in FIG. 1 is a wide band spectrum. FIG. 8 illustrates a model waveform of an interference signal in the case where the light source illustrated in FIG. 1 has two narrow band spectra separated from each other. FIG. 9 illustrates a model waveform of an OCT signal in the case where the phase difference between two light source spectra illustrated in FIG. 8 is 0. FIG. 10 illustrates a model waveform of an OCT signal in the case where the phase difference between two light source spectra illustrated in FIG. 8 is $\pi$.

As can be seen from FIG. 4 to FIG. 7, in the case of the wide band interference signal, the resolution is improved by the amount of increase in the band width in comparison with the case of the narrow band interference signal.

On the other hand, as can be seen from FIG. 8 and FIG. 9, an artifact is caused (generated) at the peak of the OCT image signal formed by using the two spectra. This artifact is generated because the envelope functions of the spectra are convoluted into the OCT signal. Thus, it is necessary to correct the envelope functions into an ideal Gaussian function by estimating and inserting a signal between the two spectra. Of course, a method can be considered in which the interpolation between the signals can be more easily performed by using two light sources respectively having two kinds of spectral information overlapping each other. However, in the spectral band to which the living body (water) has a low absorptivity, only SLDs having center wavelengths of 1.0 μm and 1.3 μm have been developed. Therefore, there is a problem that the information in the wavelength range from 1.1 μm to 1.2 μm is completely missed. Further, even if spectrum bands overlapping with each other are obtained, the artifact is generated by the discontinuity of the phase as will be described below.

In the case where an intermediate signal between two spectral signals is interpolated, when there is a phase difference between the two spectral signals, an artifact is similarly generated. When Fourier transformation of the interference signals is performed by shifting the phase of each of the interference signals, an artifact is generated so as to cause an oscillation at the peak of the OCT signal, as can be seen from the case illustrated in FIG. 9 where the phase difference between two spectra is 0, and from the case illustrated in FIG. 10 where the phase difference between two spectra is $\pi$.

In order to suppress the generation of the artifact due to this phase difference, in the arithmetic operation section 20 according to the present embodiment, the phases of the signals obtained from the separated spectral bands are made continuous by the second interference wave data correcting section 25, and then the signals are combined with each other in the corrected composite interference wave generating section 26.

(2) Intensity correction:

On the other hand, an artifact is generated around the peak of the OCT signal only by matching the phases of the signals with each other. Thus, in the arithmetic operation section 20 according to the present embodiment, the generation of the artifact around the peak of the OCT signal is suppressed in such a manner that the envelop of the corrected composite interference wave is subjected to multiplication correction in the corrected composite interference wave generating section 26.

Figure 11:
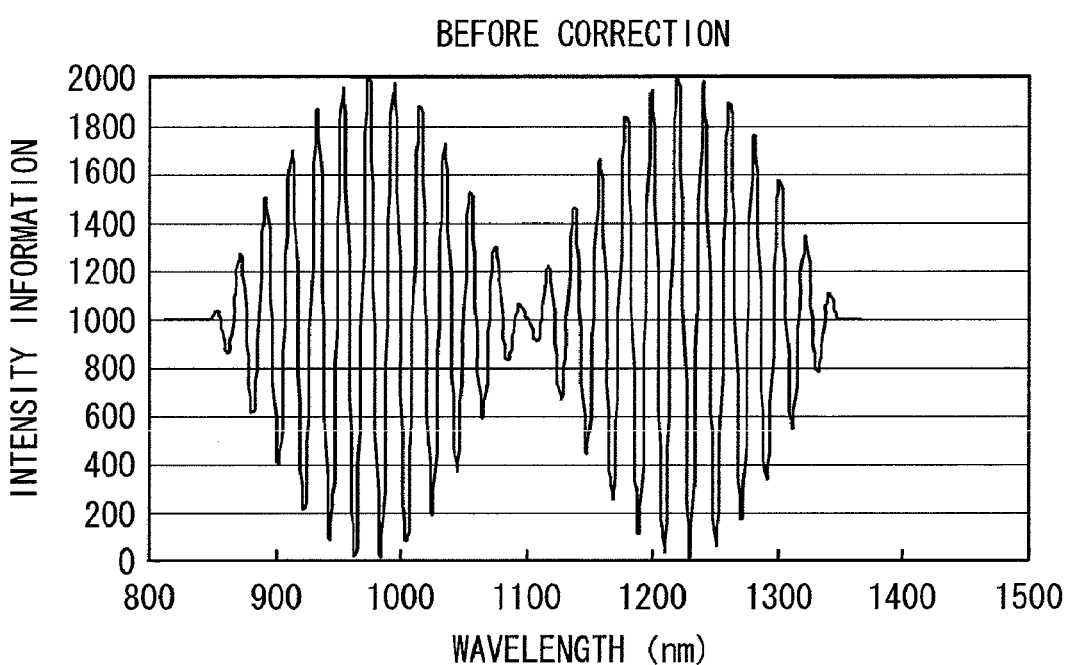
FIG. 11 illustrates model waveforms of corrected composite interference waves generated in the corrected composite interference wave generating section illustrated in FIG. 3.
Figure 12:
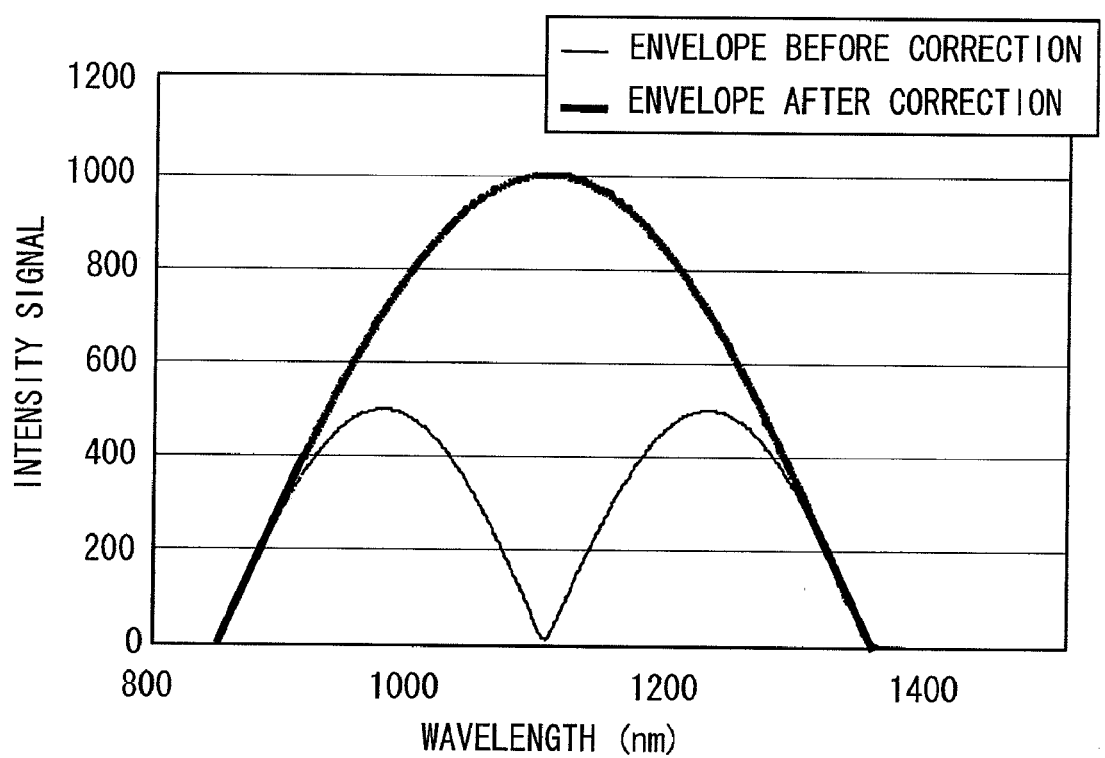
FIG. 12 is a figure for explaining envelope correction of the corrected composite interference waves illustrated in FIG. 11.

FIG. 11 illustrates model waveforms of corrected composite interference waves generated in the corrected composite interference wave generating section illustrated in FIG. 3. FIG. 12 is a figure for explaining the envelope correction of the corrected composite interference waves illustrated in FIG. 11.

As illustrated in FIG. 11, the phase of the corrected composite interference waves are made continuous by the phase correction, and the envelope of the corrected composite interference waves are configured by envelopes 700A and 700B as illustrated in FIG. 12. These envelopes 700A and 700B are calculated as intensity information by the intensity information/phase information calculating section 24.

Thus, the corrected composite interference wave generating section 26 calculates a multiplication coefficient from the two kinds of intensity information 700A and 700B. Then, the corrected composite interference wave generating section 26 corrects the corrected composite interference wave with the calculated multiplication coefficient, and thereby generates a corrected composite interference wave having an ideal envelope 701. In the corrected composite interference wave having the envelope 701, the generation of artifact around the peak of the OCT signal is reduced. The corrected composite interference wave generating section 26 suppress the generation of artifact by bringing the envelope 701 close to the ideal Gaussian shape.

Figure 13:
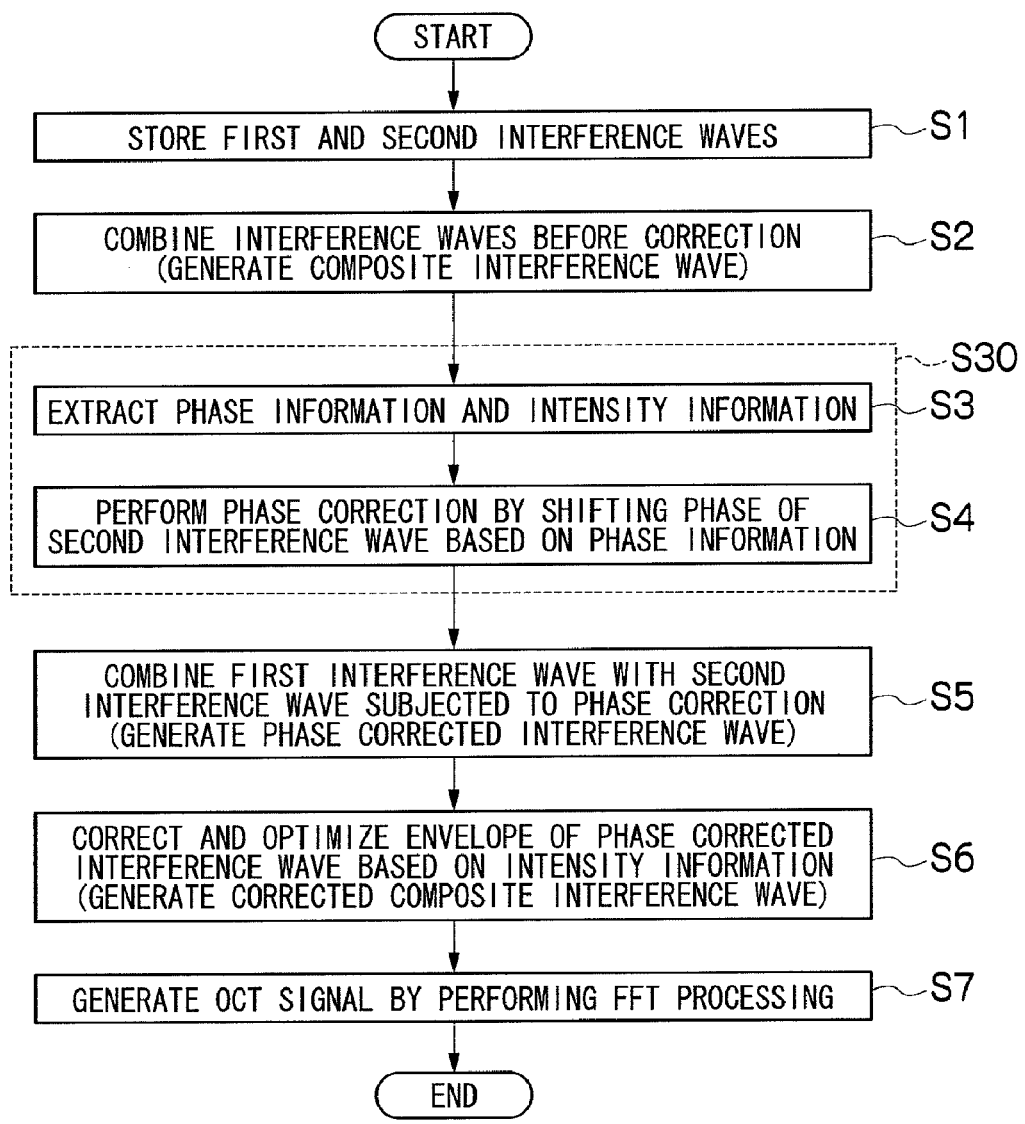
FIG. 13 is a flow chart for explaining a flow of processing in the arithmetic operation section illustrated in FIG. 3.

Next, a flow of specific processing performed in the arithmetic operation section 20 according to the present embodiment will be described. FIG. 13 is a flow chart for explaining the flow of processing of the arithmetic operation section illustrated in FIG. 3.

As illustrated in FIG. 13, the arithmetic operation section 20 stores the digital data of the interference signal ISa in the first interference wave data storage section 21, and stores the digital data of the interference signal ISb in the second interference wave data storage section 22 (step S1).

Then, the arithmetic operation section 20 combines, for each of the wavelength bands, the digital data of the interference signal ISa stored in the first interference wave data storage section 21, with the digital data of interference signal ISb stored in the second interference wave data storage section 22, so as to generate a composite interference wave (composite interference signal) (step S2).

Then, in the arithmetic operation section 20, the intensity information/phase information calculating section 24 calculates, as phase information, a phase difference of the second interference wave data with respect to the first interference wave data from the composite interference wave generated by the composite interference wave generating section 23, and calculates the intensity information of the envelope of the composite interference wave (step S3).

Then, in the arithmetic operation section 20, the second interference wave data correcting section 25 performs correction to shift the phase of the second interference wave data based on the phase information calculated by the intensity information/phase information calculating section 24 (step S4).

Next, in the arithmetic operation section 20, the corrected composite interference wave generating section 26 combines, for each of the wavelength bands, the first interference wave data (interference signal ISa) stored in the first interference wave data storage section 21 with the second interference wave data (interference signal ISb) corrected by the second interference wave data correcting section 25, so as to generate a corrected composite interference wave (corrected composite signal) (step S5).

Further, in the arithmetic operation section 20, the corrected composite interference wave generating section 26 corrects the envelope (signal intensity) of the corrected composite interference wave based on the intensity information calculated by the intensity information/phase information calculating section 24 (step S6).

Then, in the arithmetic operation section 20, the FFT section 27 performs fast Fourier transform (FFT) of the corrected composite interference wave which is generated and subjected to the phase and envelope (signal intensity) correction by the corrected composite interference wave generating section 26, and generates tomographic image information (OCT image) of the measuring object S, so as to make the OCT image displayed in the display apparatus 11 (step S7).

As described above, in the present embodiment, (1) after the phase information of the interference waves is extracted, the phase of the interference waves are adjusted so that the phase difference between the interference waves becomes 0. (2) Then, the composite interference wave is multiplied by a correction coefficient so as to have an envelope of a Gaussian shape. Thus, the corrected composite interference wave obtained in this way has continuous phase and intensity information. Thereby, the arithmetic operation section 20 can acquire an FFT signal without artifact by performing FFT of the corrected composite interference wave in the FFT section 27.

Figure 14:
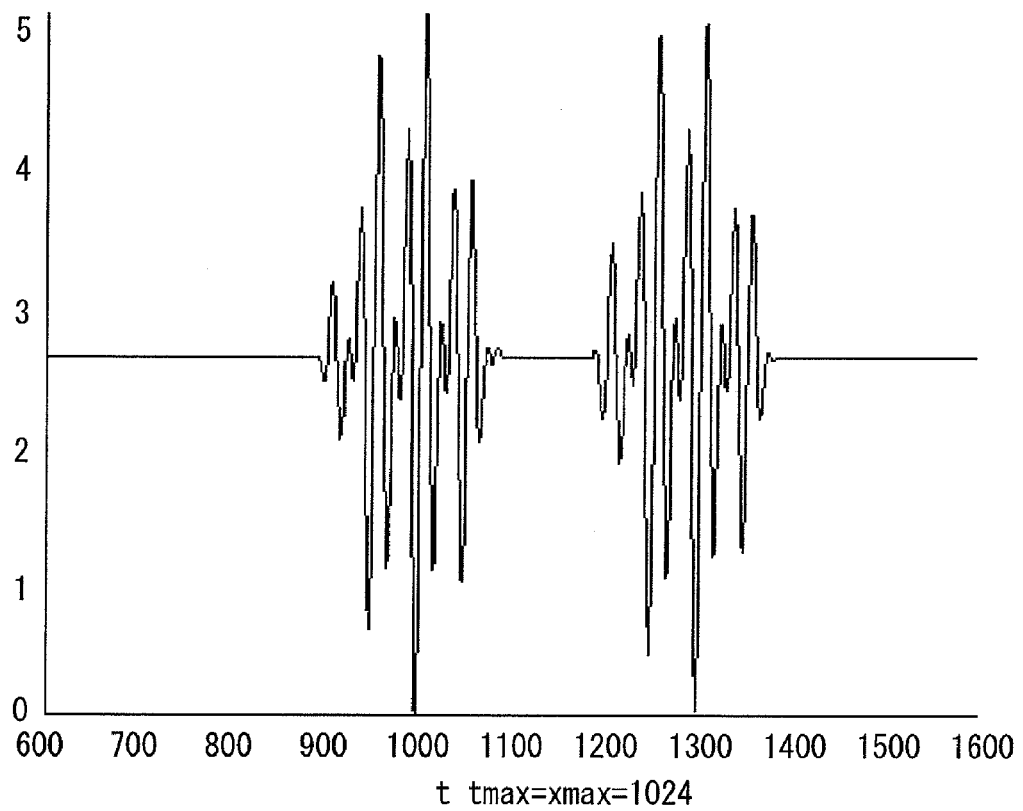
FIG. 14 is a first figure for explaining a modification of the processing in the arithmetic operation section illustrated in FIG. 3.
Figure 15:
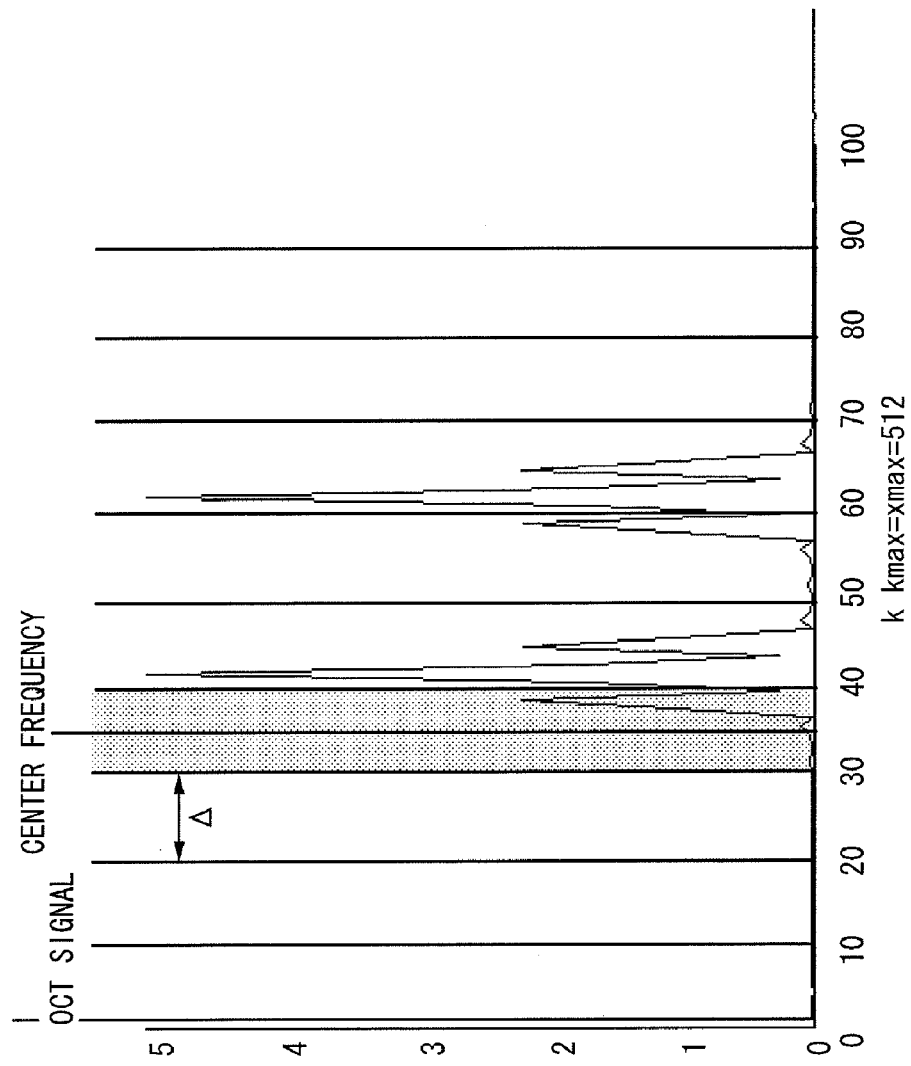
FIG. 15 is a second figure for explaining the modification of the processing in the arithmetic operation section illustrated in FIG. 3.
Figure 16:
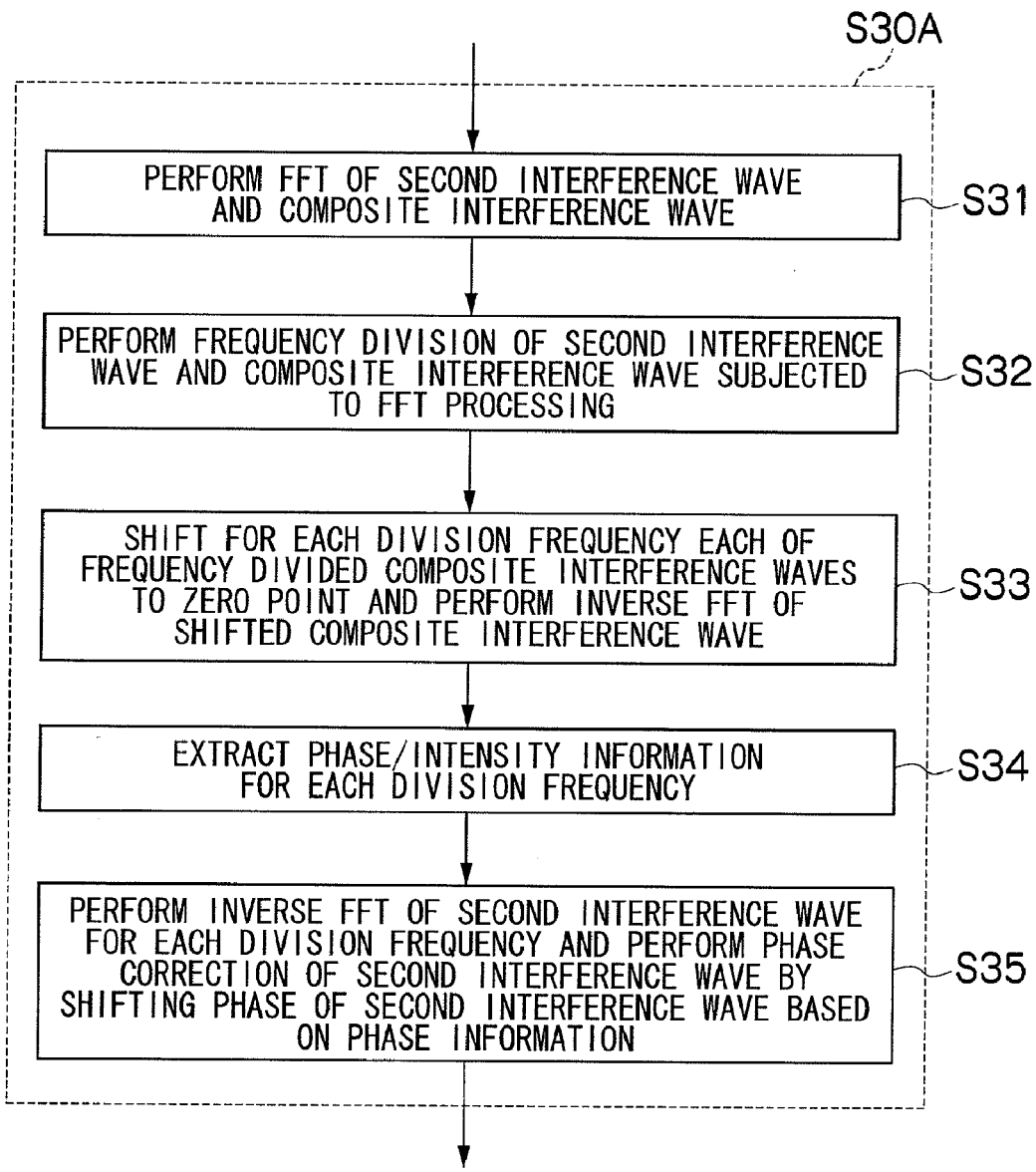
FIG. 16 is a flow chart illustrating a major portion of the flow of the modification of the processing in the arithmetic operation section illustrated in FIG. 3.

Modification:
Next, a modification of the present embodiment will be described. FIG. 14 is a first figure for explaining a modification of the processing in the arithmetic operation section illustrated in FIG. 3. FIG. 15 is a second figure for explaining the modification of the processing in the arithmetic operation section illustrated in FIG. 3. FIG. 16 is a flow chart illustrating a major portion of the flow of the modification of the processing in the arithmetic operation section illustrated in FIG. 3.

An actual OCT signal is formed by a combination of interference signals having various frequencies. Thus, as illustrated in FIG. 14, the input signal, which is the interference signal, includes phase information in each of the frequency components. For this reason, it is necessary to extract the phase information in each frequency in order to make the phase of the actual OCT image continuous by multiplexing.

Thus, in the present modification, the arithmetic operation section 20 performs FFT of the composite interference wave (composite interference signal) in order to calculate the phase information in each frequency component. Then, as illustrated in FIG. 15, the arithmetic operation section 20 divides the composite interference wave (composite interference signal), subjected to FFT processing, into division regions $\Delta$ of fixed frequency intervals, and extracts the phase information within each of the division regions $\Delta$ from each of the divided composite interference waves. Note that the signal dividing device is configured in the arithmetic operation section 20.

Specifically, in order to calculate the phase information, the arithmetic operation section 20 deletes all signals other than the signals in a division region $\Delta$, and thereafter calculates the intensity and phase information in the division region $\Delta$, for example, by shifting the center frequency of the division region $\Delta$ to the zero point and performing inverse FFT of the signals in the division region $\Delta$.

The flow of the processing performed by the arithmetic operation section 20 in the present modification will be described with reference to FIG. 16. In the present modification, the arithmetic operation section 20 performs step S30A consisting of steps S31 to S35 illustrated in FIG. 16 instead of step S30 consisting of steps S3 and S4 illustrated in FIG. 13.

That is, after performing the processing of step S2 illustrated in FIG. 13, the arithmetic operation section 20 performs FFT of the second interference wave data (interference signal ISb) and the composite interference wave (composite interference signal) (step S31).

Then, the arithmetic operation section 20 divides the second interference wave data (interference signal ISb) and the composite interference wave (composite interference signal), which are subjected to the FFT processing, into division regions $\Delta$ set at fixed frequency intervals (step S32).

Next, the arithmetic operation section 20 deletes all the signals in the composite interference wave (composite interference signal) subjected to the FFT processing other than signals included in each one of the division regions $\Delta$. Then, for the each one division region $\Delta$, the arithmetic operation section 20 shifts the center frequency of the division region $\Delta$ to the zero point and performs inverse FFT of the signals in the division region $\Delta$ (step S33).

Subsequently, the arithmetic operation section 20 calculates the phase information and intensity information from the composite interference wave (composite interference signal) shifted to the zero point for each one of the division regions $\Delta$(step S34).

Then, the arithmetic operation section 20 performs inverse FFT of the second interference wave data (interference signal ISb) for each one of the division regions $\Delta$, and corrects the phase of the second interference wave data based on the calculated phase information (step S35). Then, the arithmetic operation section 20 shifts the processing to step S5 illustrated in FIG. 13.

Figure 17:
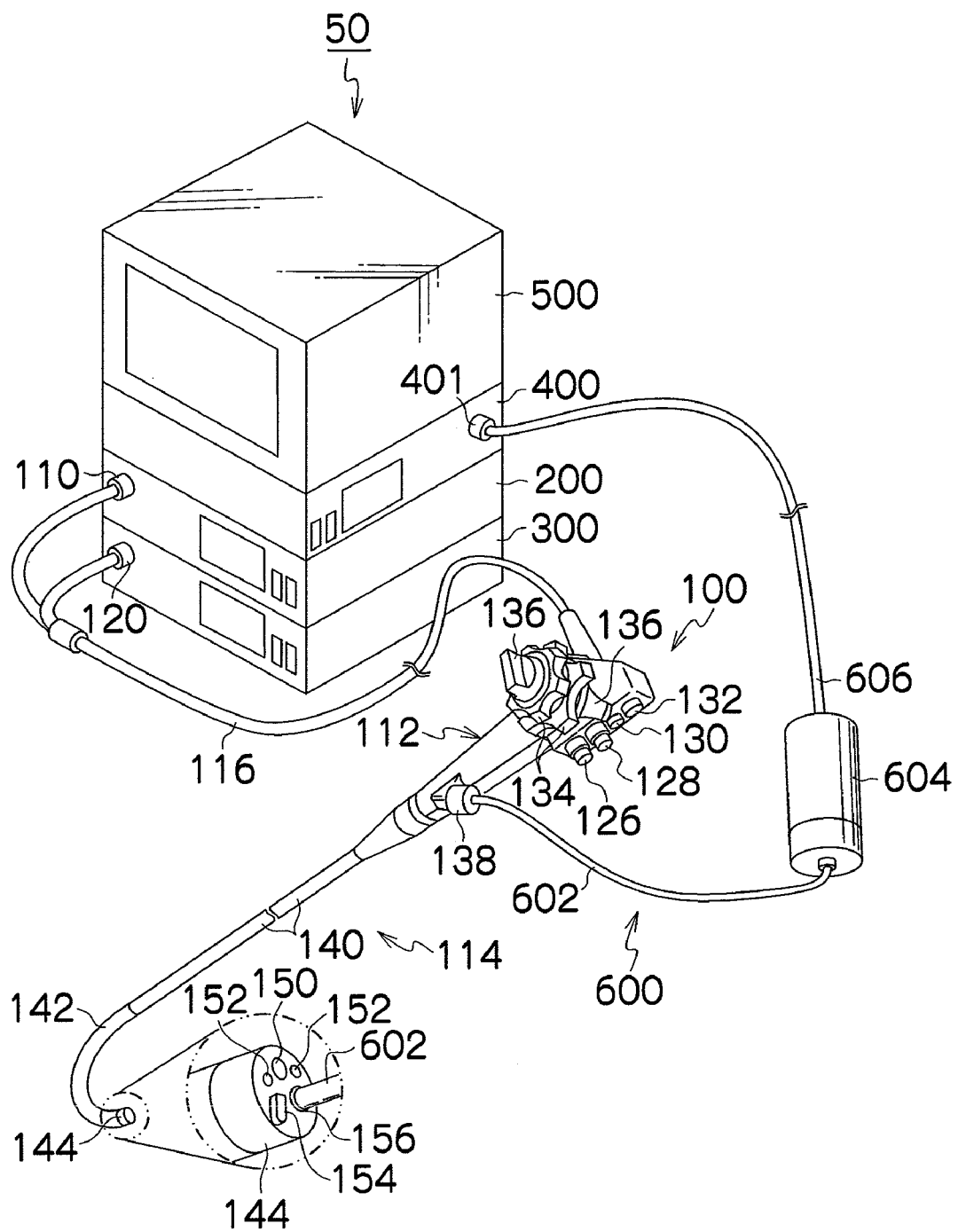
FIG. 17 illustrates an image diagnostic apparatus used together with an endoscope apparatus to which the OCT probe of the optical tomographic imaging apparatus illustrated in FIG. 1 can be applied.

Note that the present embodiment can be applied to a diagnostic imaging apparatus used together with an endoscope apparatus. In more detail, as illustrated in FIG. 17, a diagnostic imaging apparatus 50, in which the OCT probe 600 according to the present embodiment is used together with an endoscope apparatus, includes an endoscope 100, an endoscope processor 200, a light source apparatus 300, an OCT processor 400 serving as a living body tomographic image generating apparatus, and an image display section 500 which is a monitoring apparatus serving as a display device. Note that the endoscope processor 200 may be configured so as to incorporate therein the light source apparatus 300.

The endoscope 100 has a hand operation section 112 and an insertion section 114 continuously connected to the hand operation section 112. An operator performs observation by grasping and operating the hand operation section 112 and by inserting the insertion section 114 into the subject's body.

A forceps insertion section 138 is provided in the hand operation section 112, and is made to communicate with a forceps opening 156 of the distal end section 144 of the endoscope 100 via a forceps channel (not illustrated) provided in the insertion section 114. In the image diagnostic apparatus 50, the OCT probe 600 as a probe is inserted into the forceps channel from the forceps insertion section 138 and thereby led out from the forceps opening 156. The OCT probe 600 includes an insertion section 602 which is inserted from the forceps insertion section 138 and led out from the forceps opening 156, an operating section 604 which is used by the operator to operate the OCT probe 600, and a cable 606 which is connected to the OCT processor 400 via a connector 401.

An observation optical system 150, an illumination optical system 152, and a CCD (Charge Coupled Device Image Sensor, not illustrated) are arranged at the distal end section 144 of the endoscope 100.

The observation optical system 150 forms an image of the subject on a light receiving surface of the CCD (not illustrated), and the CCD converts the subject image formed on the light receiving surface thereof to electric signals by respective light receiving elements. The CCD of the present embodiment is a color CCD in which color filters of primary three colors of red (R), green (G) and blue (B) are arranged for each pixel in a predetermined arrangement (Bayer arrangement, honeycomb arrangement).

The light source apparatus 300 makes a visible light beam incident on a light guide (not illustrated). One end of the light guide is connected to the light source apparatus 300 via an LG connector 120, and the other end of the light guide faces the illumination optical system 152. The light beam emitted from the light source apparatus 300 is emitted from the illumination optical system 152 via the light guide, so as to illuminate the visual field range of the observation optical system 150.

An image signal outputted from the CCD is inputted into the endoscope processor 200 via an electric connector 110. In the endoscope processor 200, this analog image signal is converted into a digital image signal and subjected to processing necessary for being displayed on the screen of the image display section 500.

In this way, the data of the observed image obtained with the endoscope 100 is outputted to the endoscope processor 200, and an image is displayed in the image display section 500 connected to the endoscope processor 200.

As described above, an optical tomographic imaging apparatus, an interference signal processing method, and an endoscope apparatus according to the presently disclosed subject matter are described. However, it is obvious that the presently disclosed subject matter is not limited to the above described embodiments, and various modifications and variations are possible within the scope and spirit of the presently disclosed subject matter.

What is claimed is:

1. An optical tomographic imaging apparatus comprising:
a light source unit configured to emit a plurality of luminous fluxes respectively having predetermined wavelength bands different from each other by sweeping wavelength in each of the predetermined wavelength bands;
a light dividing device configured to divide, into a measuring light beam and a reference light beam, each of the plurality of luminous fluxes emitted from the light source unit;
a plurality of interference light detecting devices, when a plurality of measuring light beams divided by the light dividing device are irradiated onto a measuring object, each of the plurality of interference light detecting devices detecting, for each of the luminous fluxes, an interference light signal between a reflected light beam from the measuring object and the reference light beam;
a composite interference signal generating device configured to generate a composite interference signal formed by combining a plurality of interference light signals detected by the interference light detecting devices;
an interference information calculating device configured to calculate phase information of the plurality of interference signals detected by the interference light detecting devices based on the composite interference signal, the interference information calculating device configured to calculate signal intensity information of the interference light signal based on the composite interference signal;
an interference information correcting device configured to use, as a reference, a phase of the interference light signal obtained from a luminous flux of a first wavelength band, and to generate a corrected interference light signal by correcting, based on the phase used as the reference, a phase of the interference light signal obtained from a luminous flux of a wavelength band different from the first wavelength band;
a corrected composite signal generating device configured to generate a corrected composite signal formed by combining the interference light signal of the first wavelength band and the corrected interference light signal; and
an intensity correcting device configured to correct an envelope of a signal intensity of the corrected composite signal to a Gaussian shape based on the signal intensity information of the interference light signal, the signal intensity information being calculated by the interference information calculating device.

2. The optical tomographic imaging apparatus according to claim 1, further comprising:
a tomographic image information generating device configured to generate tomographic image information of the measuring object based on the corrected composite signal.

3. The optical tomographic imaging apparatus according to claim 1, further comprising
a signal dividing device configured to divide each of the interference signal and the composite interference signal based on predetermined divided wavelength widths,
wherein the interference information calculating device calculates the phase information for each of the divided wavelength widths, wherein the interference information correcting device generates the corrected interference light signal for each of the divided wavelength widths, and wherein the corrected composite signal generating device generates the corrected composite signal for each of the divided wavelength widths.

4. The optical tomographic imaging apparatus according to claim 1, wherein wavelength sweep periods are synchronized between the plurality of luminous fluxes.

5. An interference signal processing method of an optical tomographic imaging apparatus, comprising:

a light beam dividing step of dividing, into a measuring light beam and a reference light beam, each of a plurality of luminous fluxes which respectively have predetermined wavelength bands different from each other and which are emitted by sweeping wavelength in the respective predetermined wavelength bands;

an interference light detecting step of detecting, for each of the luminous fluxes, an interference light signal between the reference light beam and a reflected light beam which is reflected from a measuring object at the time when a plurality of measuring light beams formed in the light beam dividing step are irradiated onto the measuring object;

a composite interference signal generating step of generating a composite interference signal formed by combining a plurality of interference light signals detected in the interference light detecting step;

an interference information calculating step of calculating phase information of the plurality of interference light signals detected in the interference light detecting step based on the composite interference signal, and calculating signal intensity information of the interference light signal based on the composite interference signal;

an interference information correcting step of using, as a reference, a phase of the interference light signal obtained from a luminous flux of a first wavelength band, and of generating a corrected interference light signal by correcting, based on the phase used as the reference, a phase of the interference light signals obtained from a luminous fluxes of a plurality of wavelength bands different from the first wavelength band;

a corrected composite signal generating step of generating a corrected composite signal formed by combining the interference light signal of the first wavelength band and the corrected interference light signal; and an intensity correcting step of correcting an envelope of a signal intensity of the corrected composite signal to a Gaussian shape based on the signal intensity information of the interference light signal, the signal intensity information being calculated in the interference information calculating step.

6. An endoscope apparatus comprising:

the optical tomographic imaging apparatus according to claim 1; and an endoscope having a treatment instrument channel into which an optical probe for guiding the measuring light beam into a body cavity is inserted.

7. The optical tomographic imaging apparatus according to claim 3, wherein the signal dividing device divides the composite interference signal into divided composite interference signals for division regions of fixed frequency intervals, and the interference information calculating device extracts the phase information within each of the division regions from each of the divided composite interference signals.

8. The optical tomographic imaging apparatus according to claim 7, wherein after the interference information calculating device deletes all signals other than the signals in a division region, the interference information calculating device calculates an intensity and phase information in the division region, by shifting a center frequency of the division region to a zero point and performing inverse Fast Fourier Transform of the signals in the division region.

9. The interference signal processing method of an optical tomographic imaging apparatus according to claim 5, further comprising a signal dividing step of dividing each of the interference signal and the composite interference signal based on predetermined divided wavelength widths, wherein the phase information for each of the divided wavelength widths is calculated in the interference information calculating step, wherein the corrected interference light signal for each of the divided wavelength widths is generated in the interference information correcting step, and wherein the corrected composite signal for each of the divided wavelength widths is generated in the corrected composite signal generating step.

10. The interference signal processing method of an optical tomographic imaging apparatus according to claim 9, wherein the composite interference signal is divided into divided composite interference signals for division regions of fixed frequency intervals in the signal dividing step, and the phase information within each of the division regions is extracted from each of the divided composite interference signals in the interference information calculating step.

11. The interference signal processing method of an optical tomographic imaging apparatus according to claim 10, wherein the interference information calculating step comprises:

deleting all signals other than the signals in a division region; and calculating an intensity and phase information in the division region, by shifting a center frequency of the division region to a zero point and performing inverse Fast Fourier Transform of the signals in the division region.

* * * * *